(12) United States Patent
King

(10) Patent No.: US 8,469,050 B2
(45) Date of Patent: Jun. 25, 2013

(54) CAPACITIVE FLUID LEVEL SENSING

(75) Inventor: David A King, Pleasanton, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 297 days.

(21) Appl. No.: 12/267,214

(22) Filed: Nov. 7, 2008

(65) Prior Publication Data
US 2010/0121257 A1   May 13, 2010

(51) Int. Cl.
*F16K 21/18* (2006.01)
(52) U.S. Cl.
USPC .................................... 137/392; 604/319
(58) Field of Classification Search
USPC .................... 137/392; 604/119, 319, 323
See application file for complete search history.

(56) References Cited

U.S. PATENT DOCUMENTS

| | | | | |
|---|---|---|---|---|
| 4,464,172 A | * | 8/1984 | Lichtenstein | 604/65 |
| 4,475,904 A | * | 10/1984 | Wang | 604/119 |
| 4,626,248 A | * | 12/1986 | Scheller | 604/319 |
| 4,713,051 A | * | 12/1987 | Steppe et al. | 604/30 |
| 4,756,238 A | * | 7/1988 | Naruse et al. | 92/65 |
| 4,773,897 A | * | 9/1988 | Scheller et al. | 604/34 |
| 4,790,816 A | * | 12/1988 | Sundblom et al. | 604/31 |
| 5,125,891 A | * | 6/1992 | Hossain et al. | 604/34 |
| 5,135,485 A | | 8/1992 | Cohen et al. | |
| 5,324,180 A | * | 6/1994 | Zanger | 417/477.1 |
| 5,342,293 A | * | 8/1994 | Zanger | 604/22 |
| 5,364,342 A | * | 11/1994 | Beuchat et al. | 604/30 |
| 5,568,395 A | * | 10/1996 | Huang | 716/102 |
| 5,582,601 A | * | 12/1996 | Wortrich et al. | 604/318 |
| 5,700,240 A | * | 12/1997 | Barwick et al. | 604/22 |
| 5,733,256 A | * | 3/1998 | Costin | 604/22 |
| 6,971,076 B2 | * | 11/2005 | Chen | 716/115 |
| 7,107,837 B2 | * | 9/2006 | Lauman et al. | 73/304 C |
| 7,326,183 B2 | * | 2/2008 | Nazarifar et al. | 604/30 |
| 7,594,901 B2 | * | 9/2009 | Hopkins et al. | 604/65 |
| 2005/0172712 A1 | * | 8/2005 | Nyce | 73/304 C |
| 2005/0245888 A1 | * | 11/2005 | Cull | 604/317 |
| 2006/0200068 A1 | * | 9/2006 | Kadziauskas et al. | 604/22 |
| 2007/0005029 A1 | | 1/2007 | Hopkins et al. | |
| 2008/0112828 A1 | * | 5/2008 | Muri et al. | 417/477.2 |
| 2008/0112842 A1 | * | 5/2008 | Edwards | 422/2 |
| 2008/0112889 A1 | * | 5/2008 | Buggy et al. | 424/9.2 |
| 2008/0114290 A1 | * | 5/2008 | King et al. | 604/30 |

(Continued)

FOREIGN PATENT DOCUMENTS

| EP | 1384945 A1 | 1/2004 |
|---|---|---|
| EP | 1469895 B1 | 4/2008 |

(Continued)

*Primary Examiner* — Craig Schneider
*Assistant Examiner* — Craig J Price
(74) *Attorney, Agent, or Firm* — Abbott Medical Optics Inc.

(57) ABSTRACT

A capacitive fluid level sensing arrangement for use in a medical device is provided. The arrangement includes at least one pair of conductive plates configured to increase and decrease the amount of electric charge stored in relation to the level of fluid within a fluid maintaining device, such as a reservoir. The conductive plates are electrically connected to a medical device and are configured to measure the charge stored between the plates and thus sense the fluid level. The electric circuit may communicate the measurement to an instrument host arrangement for operating a pump configured to remove fluid from the reservoir and move the fluid to a collector when the level exceeds a preset upper level amount. The instrument host arrangement may stop operating the pump when the fluid level is reduced to a preset lower level amount.

32 Claims, 12 Drawing Sheets

U.S. PATENT DOCUMENTS

| | | | |
|---|---|---|---|
| 2008/0114291 A1* | 5/2008 | Muri et al. | 604/35 |
| 2008/0114300 A1* | 5/2008 | Muri et al. | 604/131 |
| 2008/0114301 A1* | 5/2008 | Bandhauer et al. | 604/153 |
| 2008/0114311 A1* | 5/2008 | Muri et al. | 604/294 |
| 2008/0114312 A1* | 5/2008 | Muri et al. | 604/294 |
| 2008/0114372 A1* | 5/2008 | Edwards et al. | 604/30 |
| 2008/0125698 A1* | 5/2008 | Gerg et al. | 604/35 |
| 2009/0048607 A1* | 2/2009 | Rockley | 606/107 |
| 2010/0249693 A1* | 9/2010 | Links | 604/22 |
| 2010/0280434 A1* | 11/2010 | Raney et al. | 604/22 |
| 2010/0280435 A1* | 11/2010 | Raney et al. | 604/22 |

FOREIGN PATENT DOCUMENTS

| | | |
|---|---|---|
| GB | 2040464 A | 8/1980 |
| WO | 2007062714 A1 | 6/2007 |
| WO | WO 2008119993 A1 | 10/2008 |

\* cited by examiner

CAPACITIVE FLUID LEVEL SENSING

BACKGROUND OF THE INVENTION

1. Field of the Invention

The present invention relates generally to the field of ocular surgery, and more specifically to managing fluid levels within a reservoir using a capacitive sensor device for measuring the reservoir fluid level during ophthalmic procedures such as the removal of a cataract.

2. Description of the Related Art

Phacoemulsification surgery has been successfully employed in the treatment of certain ocular problems, such as cataract surgery, including removal of a cataract-damaged lens and implanting an artificial intraocular lens. Phacoemulsification surgery typically involves removal of the cataract-damaged lens and may utilize a small incision at the edge of the patient's cornea. Through the small incision, the surgeon then creates an opening in the capsule, i.e. membrane that encapsulates the lens.

Next, the surgeon may insert an ultrasonic probe, incorporated within the phacoemulsification handpiece, through the opening in the cornea and capsule accessing the damaged lens. The handpiece's ultrasonic actuated tip emulsifies the damaged lens sufficient to be evacuated by the handpiece. After the damaged natural lens is completely removed, the handpiece tip is withdrawn from the patient. The surgeon may now implant an intraocular lens into the space made available in the capsule.

While performing phacoemulsification surgical techniques, such as lens removal, the surgeon may control a pump to pull fluids from the eye and through the handpiece tip. The pump is configured with a tank or reservoir positioned to hold the fluid until the tank fills to a certain point or level. During emulsification of the damaged lens, the tip of the phaco handpiece may collect fluids from the patient's eye and transfer the fluids for holding or temporarily storing in the reservoir. As the tip further collects fluid and material, the reservoir may fill with fluid to a point where the ratio of the volume of air with respect to the volume of fluid in the reservoir is outside of a desirable operating range. Typically, the desired operating range may dictate a minimum volume required for venting and reflux, a maximum volume to prevent the pump from exposure to fluids or from working into an uncompressible volume, and an intermediate or target volume representing a desired air-to-fluid ratio. During an ocular procedure, the air-to-fluid ratio may reach a point where the reservoir requires "rebalancing," which involves adding fluid to, or removing fluid from, the reservoir for the purpose of maintaining the desired operational ratio.

During the surgery it may become necessary for the surgeon to be able to remove fluid from a reservoir, or tank, into a waste or collection bag for the purpose of rebalancing the reservoir. One method for rebalancing the reservoir, when the fluid level exceeds the desirable operating range, involves the outflow of fluid and materials from the reservoir into a collection bag using a pump. When the fluid reaches a certain level the pump is turned on and removes or drains the reservoir. Alternatively, if the fluid level in the reservoir falls below a low level threshold, rebalancing may involve the inflow of fluid from the collection bag or from an infusion bottle into the reservoir. In either arrangement, when the reservoir air-to-fluid ratio is returned within desirable operating values, indicating the reservoir is 'balanced' the pump is stopped which in turn stops the flow of fluid and materials.

Maintaining a proper air-to-fluid ratio or balance within the reservoir may allow the surgeon to perform various aspiration, vacuum venting, and reflux surgical procedures without interruption. When the reservoir level reaches an upper lever threshold, thus requiring outflow or removal of fluid, the instrument host typically turns on a pump to move the fluid from the reservoir to the collection bag.

In order to remove fluid, current designs typically determine the proper time to activate a peristaltic reservoir pump by sensing the fluid level in the reservoir. Today's designs typically involve either a float mechanism, an optical or sound emitter-sensor system, using for example infrared light and ultrasonic frequencies.

Many of today's designs integrate the reservoir with other components, such as pumps, selector valves, and surgical tubing, into a surgical cassette system. The surgical cassette system is situated between the handpiece and collection bag and may provide an interface for a vacuum pump and peristaltic pump operations.

For example, Advanced Medical Optics, Inc. (AMO) of Santa Ana, Calif. offers a phacoemulsification medical system that has dual pump capability and employs a specific replaceable surgical cassette that enables dual pump operation and can be changed after a surgical procedure. A dual pump surgical cassette exhibiting an efficient reservoir fluid level sensing arrangement that can manage the reservoir's air-to-fluid ratio by controlling pump operation is highly desirable. Certain designs may include operating the opening and closing of a valve to allow gravity to empty contents from the reservoir into the collection bag in lieu of operating the pump.

Controlling mechanized fluid outflow and inflow for a surgical cassette reservoir by sensing devices that enable precise determination of the fluid level within the reservoir for operating a pump is often desirable in an operating room situation. While certain sensor devices have previously been offered, reliability in air-fluid reservoir balancing in these cassettes can at times be imperfect, particularly in precise operating environments.

Some previous designs include a float mechanism, which can fail by sticking to the side of the reservoir, or the float may "sink" into the reservoir. Optical and sound mechanisms tend to be costly to deploy, and in certain cases are unreliable when the sensing path is subjected to condensation, droplets, debris, or foam. It would be beneficial to offer a surgical cassette that employs minimal components or components that efficiently control and maintain the fluid level within the cassette reservoir as required in the ocular surgical environment.

SUMMARY OF THE INVENTION

According to one aspect of the present design, there is provided a surgical system comprising a controller configured to receive electrical signals and effectuate performance of the surgical system, a reservoir, a capacitive sensing device associated with the reservoir and configured to sense fluid level in the reservoir, and electrical connections between the controller and the capacitive sensing device. The capacitive sensing device senses changes in fluid level in the reservoir, and conveys sensed changes to the controller via the electrical connections. The controller selectively alters fluid level in the reservoir based on the sensed changes received from the capacitive sensing device via the electrical connections.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE DESIGN

Figure 1:
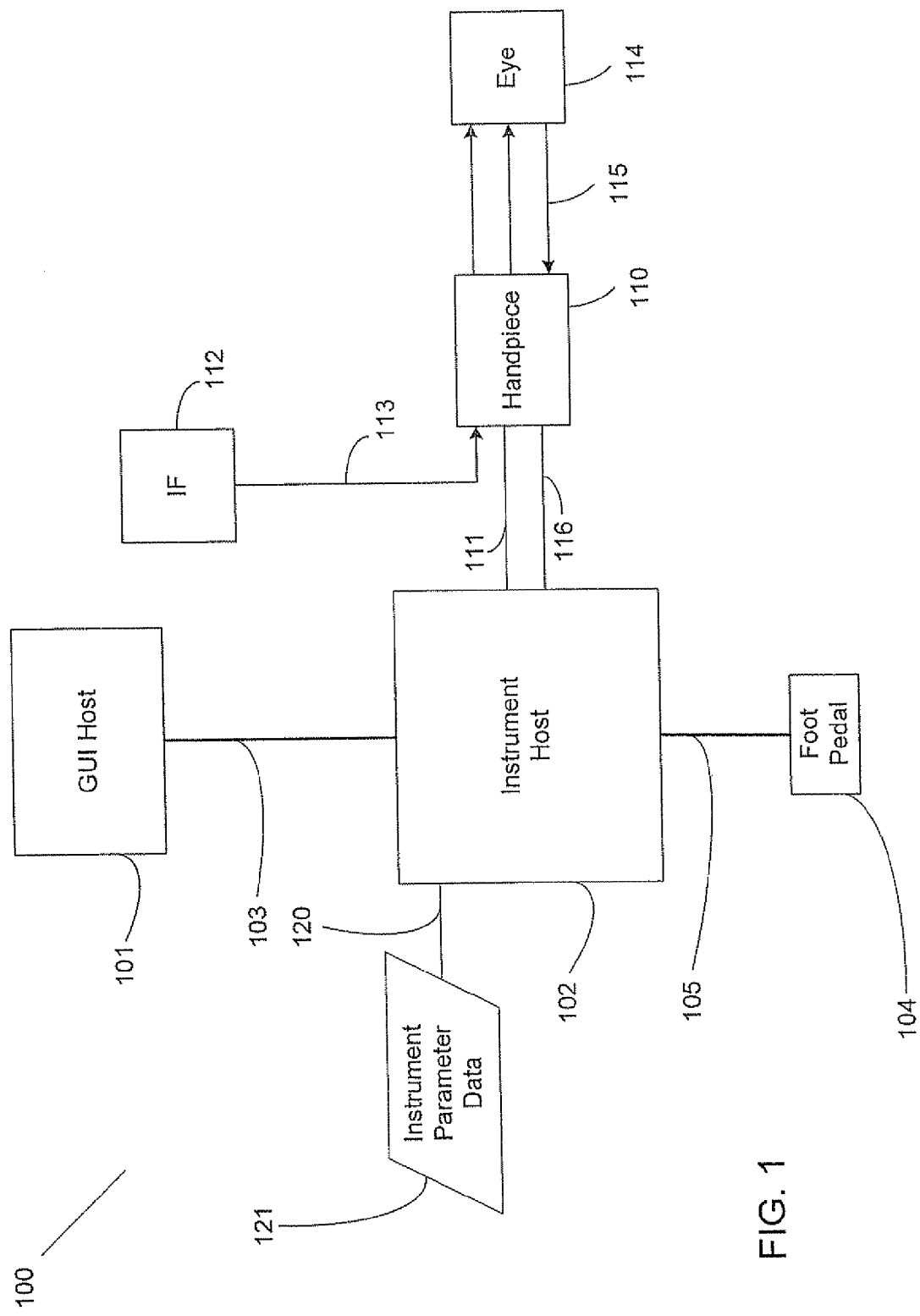
FIG. 1 illustrates an exemplary phacoemulsification/vitrectomy system in a functional block diagram to show the components and interfaces for a safety critical medical instrument system that may be employed in accordance with an aspect of the present invention.

The following description and the drawings illustrate specific embodiments sufficient to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design is directed to sensing fluid levels in a reservoir in a system, such as, but not limited to sensing the fluid level within a surgical cassette's integrated air-fluid reservoir and mechanized controlling of the fluid level within the reservoir. The present arrangement may include a device, such as a pump (peristaltic, venturi, flow or vacuum based pump, etc.), configured to provide outflow/inflow of fluid from the air-fluid reservoir and move the fluid to/from a collector such as a collection bag for purposes of maintaining proper balance of air and fluid in the reservoir. Any pump known in the art may be used with the present invention, including, but not limited to, peristaltic, venturi (wherein fluid flowing through a narrowing pipe produces vacuum as a result of the "Venturi effect"), and/or other flow or vacuum based pumps.

The present design may employ a capacitive fluid level-sensor device with the air-fluid reservoir for sensing the level of fluid within the cassette's reservoir. The capacitive fluid level-sensor device may be in any orientation with respect to a fluid maintaining device, such as a reservoir, including, but not limited to attached inside and/or outside the walls of the fluid maintaining device and/or external to the fluid maintaining device, but not attached to the device. For example, a phacoemulsification system ("phaco system") may provide for vacuum regulated aspiration, where a surgeon performing an ocular surgery may remove a large volume of fluid and material from the patient's eye. Vacuum regulated aspiration may increase the fluid level within the surgical cassette's reservoir in a relatively short amount of time. If the reservoir receives too much fluid, the level may rise above an acceptable level and may inhibit performance. For example, a rise in fluid level above certain reservoir fluid connections may cause the phaco system to operate improperly or stop.

During vacuum regulated aspiration the phaco system moves fluid from the eye to a reservoir. In order to remove fluid from the reservoir, the phaco system may operate a pump and/or valve configured to move the fluid from the reservoir and into a collector. The present design's capacitive fluid level sensing system may include an electric circuit configured to measure a change in capacitance, such as a rise in capacitance when the reservoir fluid level increases, and a fall in capacitance when the level decreases from the capacitive fluid level sensor device. The electric circuit could be configured to measure a preset maximum and/or minimum threshold, or a change rate of capacitance. The system produces a control signal to start and stop a pump situated between the reservoir and collector.

For example, the system can operate the pump to add or remove fluid from the reservoir when the level falls outside of preset thresholds, either upper or lower, and stop the pump when the level is restored within the desired operational range. A surgeon performing an ocular surgical procedure may input the desired thresholds via the instrument host system or GUI host prior to surgery. In this way, the present design may allow the surgeon to focus on the ocular procedure without the need to monitor and manually adjust the air-to-fluid ratio or balance within the reservoir.

The present design comprises a fluid level sensing arrangement that may be used with a medical instrument system, such as a phaco system. The system can be provided with a reservoir in a surgical cassette system together with a pump and/or valve to control the flow of fluid to and/or from the reservoir. Newer cassettes can support aspiration and irrigation functionality, enabling a surgeon to control the operation of the phacoemulsification/vitrectomy system handpiece.

The present design is intended to provide reliable, noninvasive, and efficient fluid level sensing in a medical instrument system for use in efficiently controlling the flow of fluids between the reservoir and the collector during an ocular procedure.

System Example

While the present design may be used in various environments and applications, it will be discussed herein with a particular emphasis on an environment where a surgeon or health care practitioner performs. For example, one embodiment of the present design is in or with a phaco system that comprises an independent graphical user interface (GUI) host module, an instrument host module, a GUI device, and a controller module, such as a foot switch, to control the phaco system.

FIG. 1 illustrates an exemplary phaco/vitrectomy system 100 in a functional block diagram to show the components and interfaces for a safety critical medical instrument system that may be employed in accordance with an aspect of the present invention. A serial communication cable 103 connects GUI host 101 module and instrument host 102 module for the purposes of controlling surgical instrument host 102 by GUI host 101. GUI host 101 and instrument host 102, as well as any other component of system 100 may be connected wirelessly. Instrument host 102 may be considered a computational device in the arrangement shown, but other arrangements are possible. An interface communications cable 120 is connected to instrument host 102 module for distributing instrument sensor data 121, and may include distribution of instrument settings and parameters information, to other systems, subsystems and modules within and external to instrument host 102 module. Although shown connected to instrument host 102 module, interface communications cable 120 may be connected or realized on any other subsystem (not shown) that could accommodate such an interface device able to distribute the respective data.

A switch module associated with foot pedal 104 may transmit control signals relating internal physical and virtual switch position information as input to the instrument host 102 over serial communications cable 105 (although foot-pedal 104 may be connected wirelessly). Instrument host 102 may provide a database file system for storing configuration parameter values, programs, and other data saved in a storage device (not shown), such as upper and lower fluid level preset thresholds for the reservoir. In addition, the database file system may be realized on GUI host 101 or any other subsystem (not shown) that could accommodate such a file system.

Phaco/vitrectomy system 100 has a handpiece 110 that includes a needle and electrical means, typically a piezoelectric crystal, for ultrasonically vibrating the needle. Instrument host 102 supplies power on line 111 to a phacoemulsification/vitrectomy handpiece 110. An irrigation fluid source 112 can be fluidly coupled to handpiece 110 through line 113. The irrigation fluid and ultrasonic power are applied by handpiece 110 to a patient's eye, or affected area or region, indicated diagrammatically by block 114. Alternatively, the irrigation source may be routed to eye 114 through a separate pathway independent of the handpiece. Aspiration is provided from eye 114 by a pump (not shown), via instrument host 102, through lines 115 and 116. A surgeon/operator may select an amplitude of electrical pulses either using handpiece 110 or via instrument host 102 and GUI host 101.

In combination with phaco system 100, the present system enables aspiration or irrigation functionality in or with the phaco system and may comprise components including, but not limited to, a flow selector valve, one or more pumps, a reservoir, and a collector, such as a collection bag or a device having similar functionality.

The fluid sensing employed is described with respect to a phaco system having dual pump capability and employing a reservoir, such as the "Signature" system available from Advanced Medical Optics, Inc., of Santa Ana, Calif. Although the present discussion references operational features and functionality in context with systems such as the AMO "Signature" System, the present design is not limited to designs involving dual pump capability or a replaceable cassette and may apply to virtually any fluid based medical design where accurate fluid level measurement is desirable.

Figure 2A:
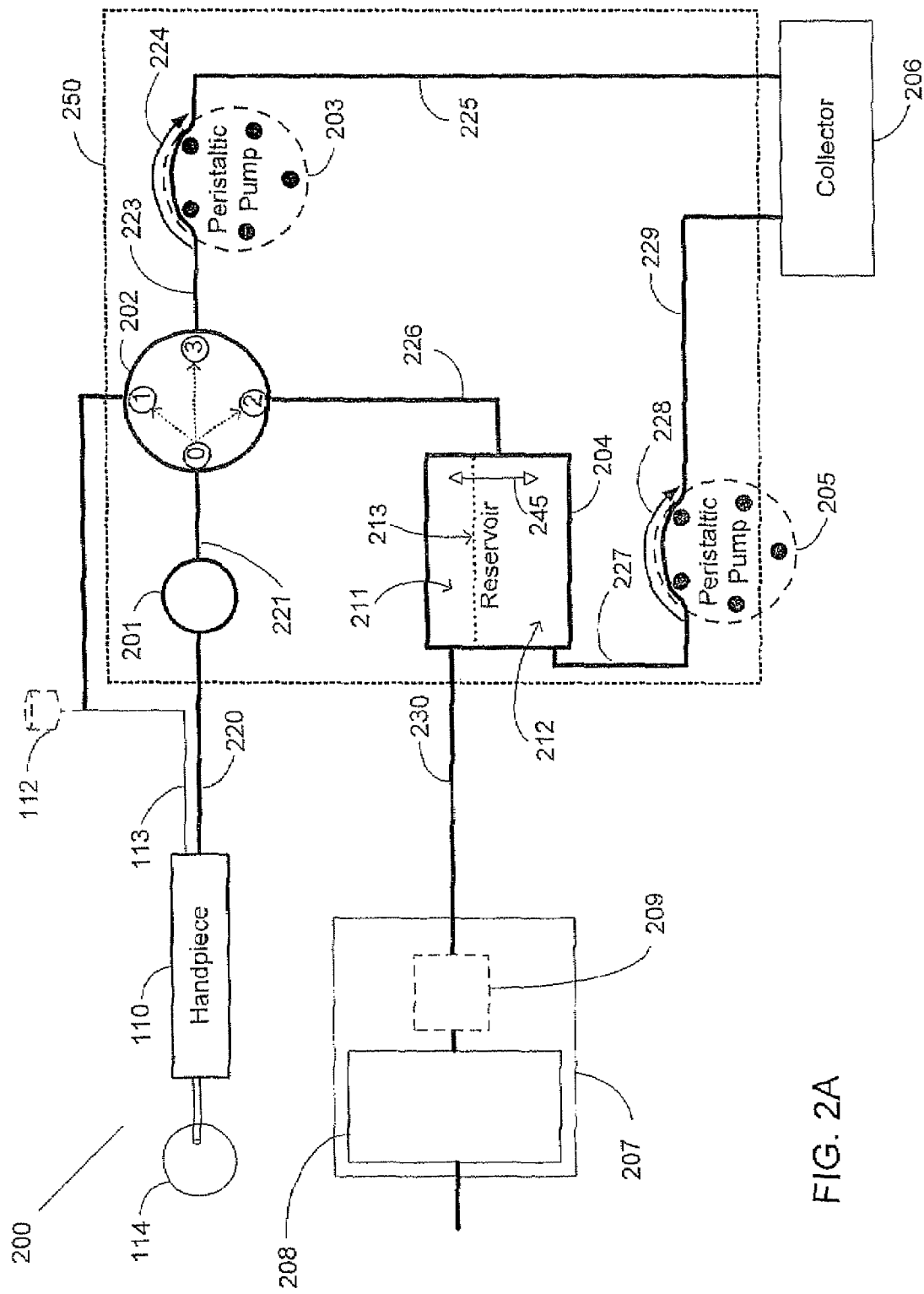
FIG. 2A illustrates an exemplary surgical system in a functional block diagram that shows the vacuum regulated aspiration components and interfaces that may be employed in accordance with an aspect of the present design.

FIG. 2A illustrates an exemplary surgical system in a functional block diagram that shows the vacuum regulated aspiration components and interfaces that may be employed in accordance with an aspect of the present design. FIG. 28 illustrates the exemplary surgical system including components and interfaces for pressure regulated infusion functions. The present design effectively connects the aspiration-infusion line from the handpiece to the air-fluid reservoir, and the reservoir is also connected to the collector through a peristaltic line. The peristaltic connection between the reservoir and collector includes a peristaltic pump configured to operate in the clockwise and counterclockwise directions.

Surgical cassette venting system 200 may include a fluid vacuum sensor 201, flow selector valve 202, reservoir 204, collector 206, and fluid pathways, such as interconnecting surgical tubing, as shown in FIG. 2. Cassette arrangement 250 may include connections to facilitate easy attachment to and removal from instrument host 102 as well as handpiece 110 and vacuum pump arrangement 207. The present design contemplates two pumps, where the surgical cassette arrangement may operate with fluid pathways or other appropriate fluid interconnections interfacing with the two pumps.

Figure 2B:
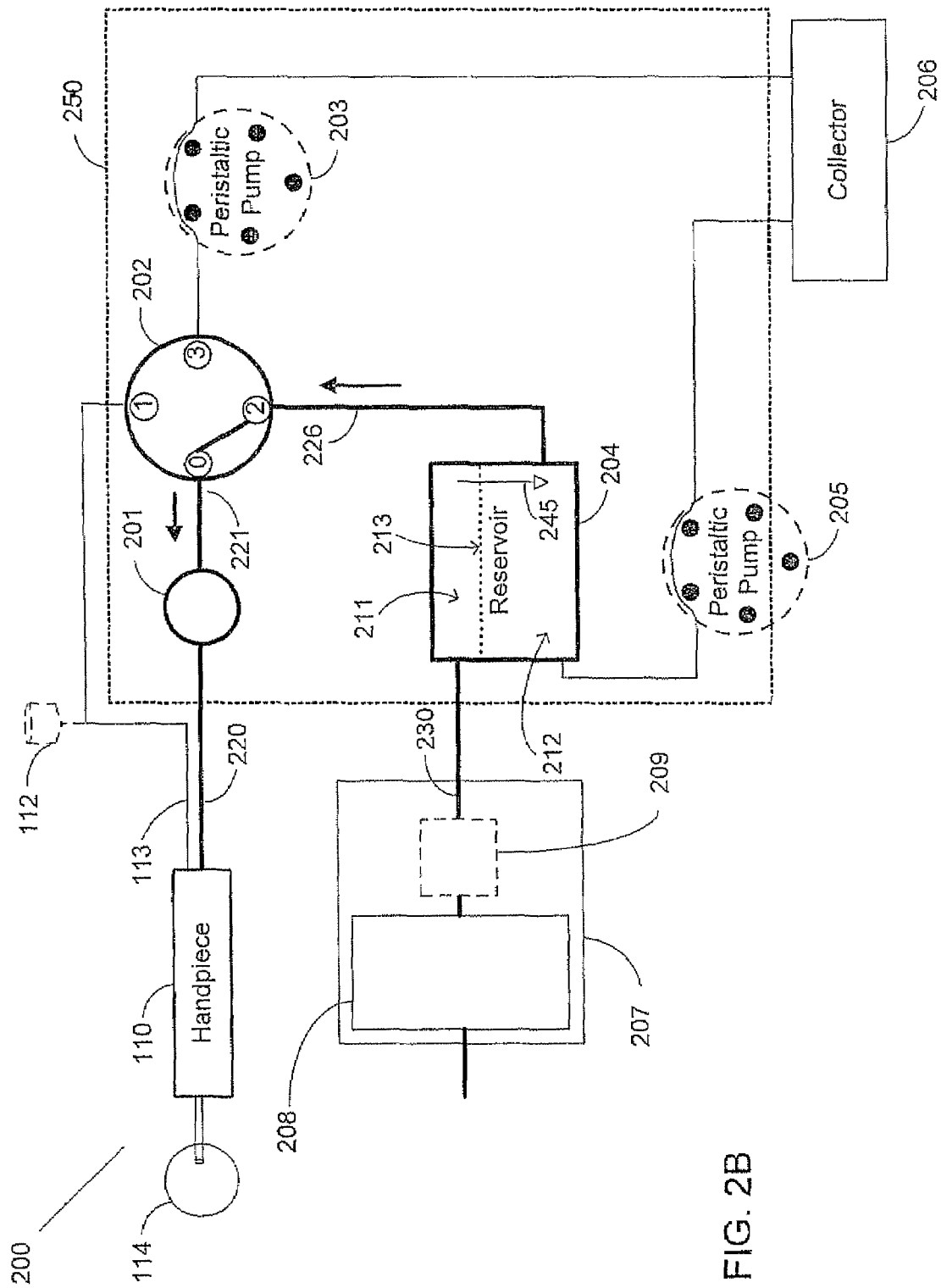
FIG. 2B illustrates an exemplary surgical system in a functional block diagram that shows the pressure regulated infusion components and interfaces that may be employed in accordance with an aspect of the present design.

Cassette arrangement 250 is illustrated in FIGS. 2A and 2B to show components that may be enclosed within the cassette. The size and shape of cassette 250 is not to scale nor accurately sized, and note that certain components, notably peristaltic pump 203, interface with the cassette but in actuality form part of the device which the cassette attaches to. Further, more or fewer components may be included in the cassette than are shown in FIGS. 2A and 2B depending on the circumstances and implementation of cassette arrangement 250.

Referring to FIG. 2A, handpiece 110 is connected to the input side of fluid vacuum sensor 201, typically by fluid pathways such as fluid pathway 220. The output side of fluid vacuum sensor 201 is connected to flow selector valve 202 within cassette arrangement 250 via fluid pathway 221. The present design may configure flow selector valve 202 to interface between handpiece 110, balanced saline solution (BSS) fluid bottle 112, pump 203, which is shown as a peristaltic pump but may be another type of pump, and reservoir 204. In this configuration, the system may operate flow selector valve 202 to connect handpiece 110 with BSS fluid bottle 112, reservoir 204 and/or with pump 203 based on signals received from instrument host 102 resulting from the surgeon's input to GUI host 101.

Flow selector valve 202 illustrated in FIGS. 2A and 2B provides a single input port and may connect port '0' to one of three available ports numbered '1', '2', and '3'. Flow selector valve 202 may also be one or more pinch valves.

Reservoir 204 may contain air in section 211 and fluid in section 212 and fluid may move up or down as indicated by arrow 245. Surgical cassette system 200 may connect reservoir 204 with collector 206 using fluid pathways, such as surgical tubing or similar items. In this arrangement, pump 205 may operate in a clockwise direction in the direction of arrow 228 to remove fluid from reservoir 204 through fluid pathway 227 and deliver the fluid to collector 206 using fluid pathway 229. The present design illustrates a peristaltic pump as pump 205, a component within instrument host 102, but other types of pumps may be employed. This configuration may enable surgical cassette 200 to remove unwanted fluid and/or material from reservoir 204. Fluid may alternately pass through fluid pathway 223 to pump 203, fluid pathway 225, and into collector 206 in certain situations.

The fluid pathways or flow segments of surgical cassette system 200 may include the fluid connections, for example flexible tubing, between each component represented with solid lines in FIGS. 2A and 2B.

Vacuum pump arrangement 207 is typically a component within instrument host 102, and may be connected with reservoir 204 via fluid pathway or flow segment 230. In the configuration shown, vacuum pump arrangement 207 includes a pump 208, such as a venturi pump and an optional pressure regulator 209 (and valve (not shown)), but other configurations are possible. In this arrangement, vacuum pump arrangement 207 may operate to remove air from the top of reservoir 204 and deliver the air to atmosphere (not shown). Removal of air from reservoir 204 in this manner may reduce the pressure within the reservoir, which reduces the pressure in the attached fluid pathway 226, to a level less than the pressure within eye 114. A lower reservoir pressure connected through flow selector valve 202 may cause fluid to move from the eye, thereby providing aspiration. Vacuum pump arrangement 207 and reservoir 204 can be used to control fluid flow into and out of reservoir 204.

The optional pressure regulator 209 may operate to add air to the top of reservoir 204 which in turn increases pressure and may force air-fluid boundary 213 to move downward. Adding air into reservoir 204 in this manner may increase the air pressure within the reservoir, which increases the pressure in the attached fluid aspiration line 226 to a level greater than the pressure within eye 114. A higher reservoir pressure connected through flow selector valve 203 may cause fluid to move toward eye 114, thereby providing venting or reflux.

FIG. 2B illustrates an optional embodiment illustrating a surgical cassette system 200 configured for venting and/or reflux operation. The FIG. 2B design may configure flow selector valve 202 to connect handpiece 110 with reservoir 204 from port '2' to port '0'. Vacuum pump arrangement 207 may operate to provide pressure to reservoir 204 via pressure regulator 209. Applying or increasing pressure using pressure regular 209 of vacuum pump arrangement 207 may move air-fluid boundary 213 downward in the direction of arrow 245 causing fluid to flow from reservoir 204 and/or fluid pathway 226 to eye 114.

Capacitive Fluid Level Sensing

The present design provides an alternative to optical fluid level sensing techniques, for example infrared sensing, and sound sensing techniques, such as ultrasonic sensing techniques. The present design includes a capacitive fluid level sensing technique wherein a capacitive fluid level-sensor device, typically a conductive plate pair forming a capacitor, is employed with a reservoir. The capacitive sensor device may connect to an electric circuit configured to measure the capacitance or electric charge stored by the capacitive sensor device, i.e. between the two conductive plates. The electric circuit may communicate the measurement as a signal to a phacoemulsification instrument host for purposes of determining the fluid level based on the measured amount of charge stored. In a further embodiment of the present design, the circuit may communicate the measurement as a signal to a separate or self-contained fluid level control circuit, such as, but not limited to that shown in FIG. 3G. Based on the level determined by the instrument host, a pump may be operated to add or remove fluid from the reservoir.

The capacitance formed between two conductive plates, arranged in accordance with the present design, may be determined by:

$$C = \in *A/d \tag{1}$$

where C is capacitance, $\in$ is permittivity of the dielectric between the two plates, A is the area of the plate, and d is the distance between conductive plates. Simply put, Equation (1) shows that capacitance is directly proportional to permittivity of the dielectric material situated between the plates. The relative permittivity of air to a vacuum is 1.00054 or approximately 1.0. The relative permittivity of water relative to a vacuum, depending on temperature, etc., is approximately 80 times greater than air, and salt water is approximately 10 times greater. The relative permittivity of the balanced salt solution (BSS) fluid used for phacoemulsification is significantly greater than air. The large difference in permittivity between air and BSS may allow the present design's capacitive fluid level sensing system to measure the fluid level in a reservoir or tank.

Arranging a capacitive fluid level-sensor device with the reservoir may store an electric charge that changes proportional to the amount of fluid stored in the reservoir. The capacitive sensing device may include parallel or planar plates that may extend from the bottom to the top of the reservoir, but may also extend to any location in between.

In the situation where the fluid level rises in the reservoir, increasing in height with respect to the conductive plates, the resulting electric charge stored between the plates increases. Conversely, as the fluid level within the reservoir falls the electric charge stored decreases. Thus continuously sensing and measuring the capacitance or electric charge stored at the present design's conductive plates arranged with the reservoir can efficiently enable determining the reservoir fluid level. In summary, the capacitance formed by the present design's plate pairs is at a minimum when the reservoir is empty, i.e. full of air, and is at a maximum when the reservoir is full, i.e. full of fluid.

FIGS. 3A-3E illustrate various exemplary embodiments for the present design capacitive fluid sensing system 300. Other configurations of the conductive plates are also envisioned by the present invention, including, but not limited to, different sizes (length, width, etc.), shapes, and/or orientations with respect to each conductive plate and/or each plate pair and with respect to the reservoir. For example, conductive plates may be positioned on opposite sides of the reservoir or at different areas within the same plane of the reservoir wall.

Figure 3A:
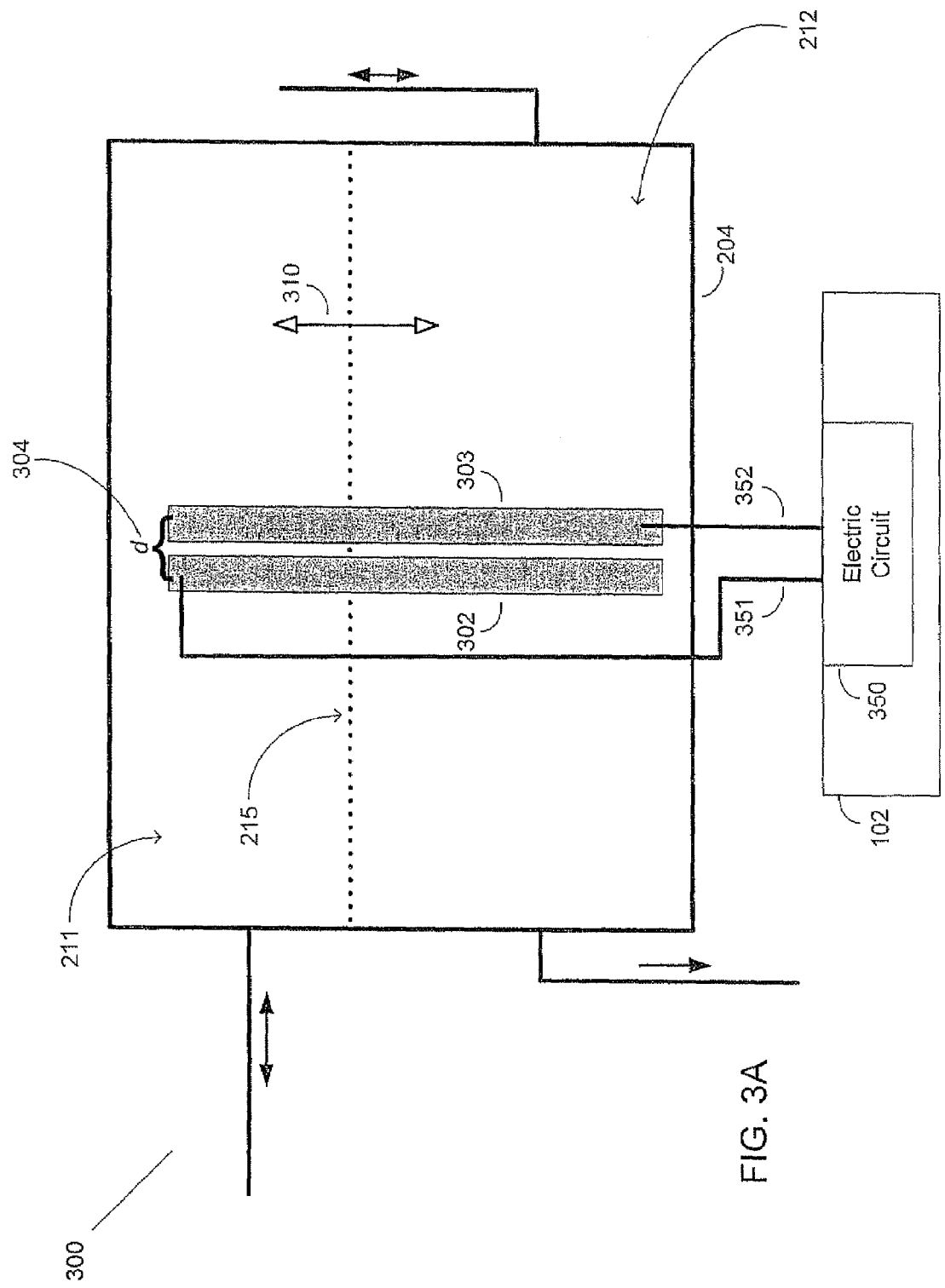
FIG. 3A illustrates a capacitive fluid level sensing system for a surgical cassette reservoir including an electric circuit where a single pair of planar plates, i.e. two conductors, forms a capacitor.
Figure 3B:
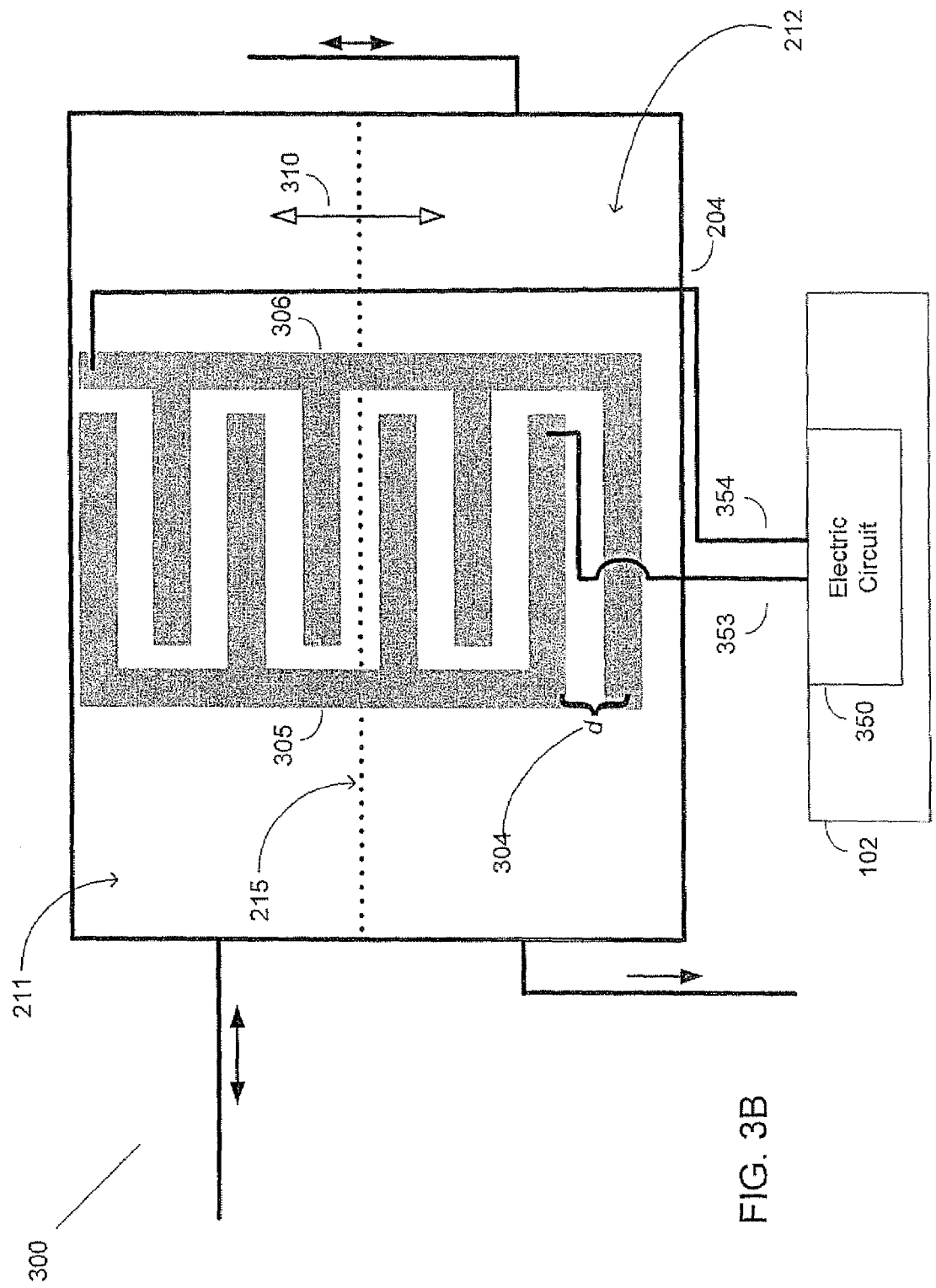
FIG. 3B illustrates a capacitive fluid level sensing system for a surgical cassette reservoir including an electric circuit where a single pair of interleaved plates, i.e. two conductors, forms a capacitor.
Figure 3C:
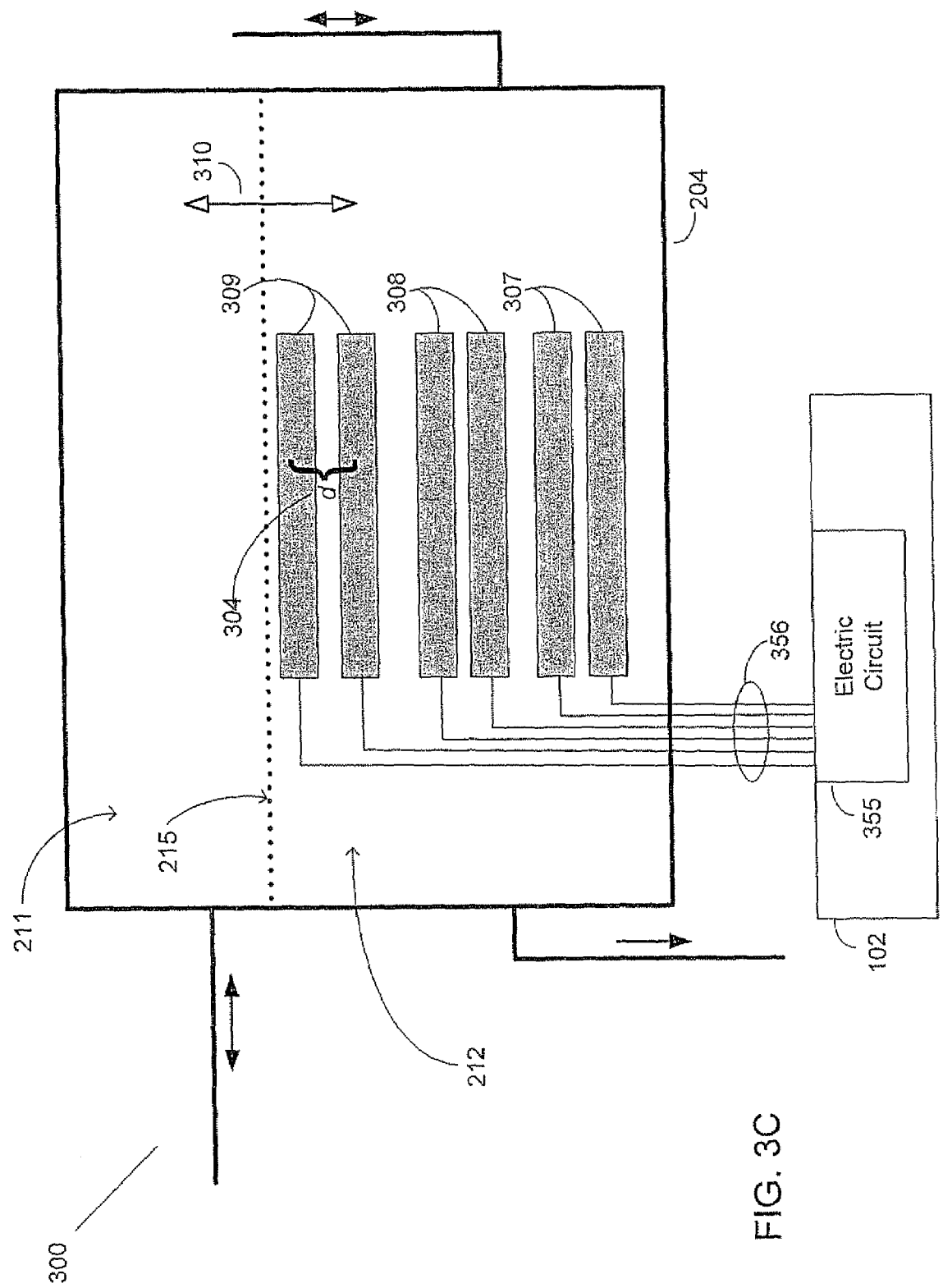
FIG. 3C illustrates a capacitive fluid level sensing system for a surgical cassette reservoir including an electric circuit where multiple planar plate pairs, i.e. two conductors, forms multiple capacitors.
Figure 3D:
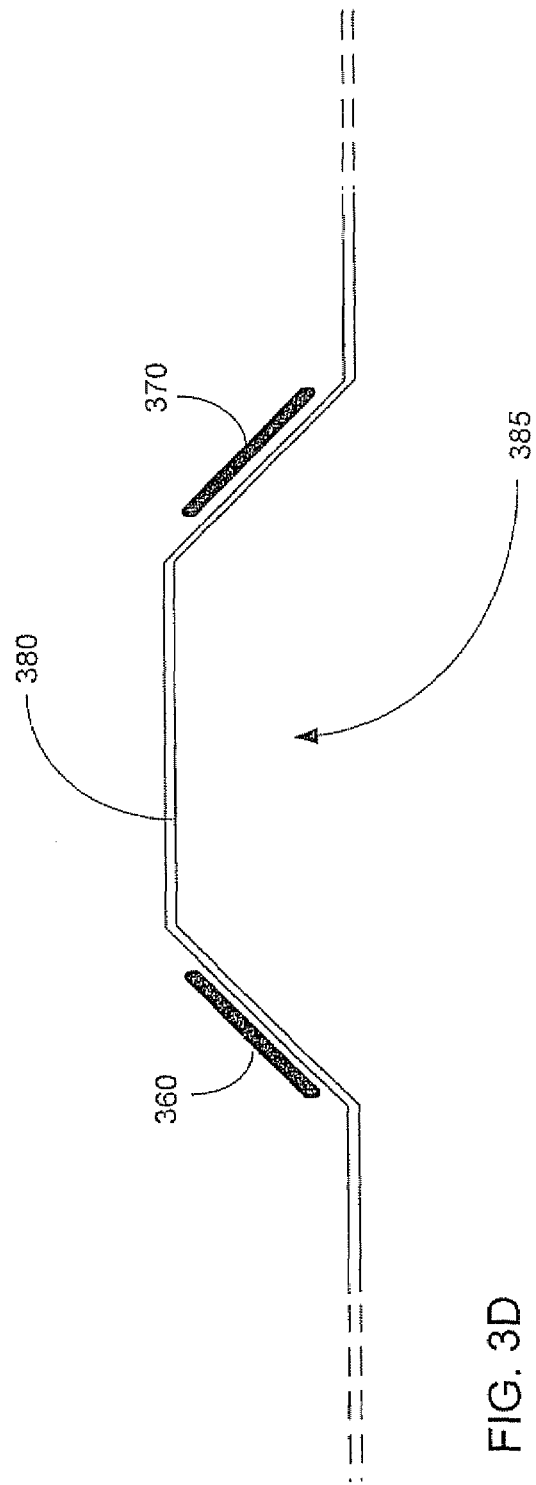
FIG. 3D illustrates the horizontal cross-section for an embodiment where an optical fluid-sensing chamber forms part of the overall evacuation chamber and a single pair of capacitive plates are positioned in close proximity to the fluid sensing chamber.

FIG. 3A shows conductive plate pairs oriented in a single plane. FIG. 3B shows interleaving of plate pairs that may provide a higher capacitance, and FIG. 3C shows multiple fluid level sensors configured at different heights. In this arrangement, the present design may provide conductive plate pairs along the walls of the reservoir, external to the reservoir, or otherwise within the reservoir for measuring fluid level in the reservoir. The present design may sense fluid level at multiple distinct heights within the reservoir by arranging plate pairs at a number of discrete points, such as at a high, middle, and a low position within the reservoir. FIG. 3D illustrates the horizontal cross-section for an existing embodiment in a representative system. In the illustrated design of FIG. 3D, an optical fluid-sensing chamber forms part of the overall evacuation chamber. The optical fluid level-sensing chamber may extend the full vertical length of the evacuation chamber, not shown in FIG. 3D.

FIG. 3A illustrates a capacitive fluid level sensing system 300 for a reservoir 204 that may be internal or external to a device such as a surgical cassette 250. Electric circuit 350 comprises a pair of plates, i.e. two conductors, forming a capacitor. The present design may orient the two plates in a parallel orientation or planar alignment with respect to each other as illustrated in FIG. 3A. The plate orientation for the present design is not limited to parallel or planar arrangements, however planar plates may provide advantages when attached in close proximity to the outside of the cassette as illustrated in FIG. 3D.

The plates notably may be part of the instrument into which the cassette including the reservoir is inserted. Plates may therefore be positioned outside the reservoir, outside the cassette, and on the instrument into which the cassette is mounted. An example of this type of mounting or operation is provided in FIG. 3D. In the case of plates attached to the reservoir, they may be inside or outside the reservoir. Preference may be outside to prevent a direct connection through conductive fluid to the electronics. If inside, the plates are electrically isolated from the fluid, such as by use of insulation or other isolating methodology known in the art.

In one embodiment, capacitive fluid level sensing system 300 includes plate 302 and plate 303 as a pair, and are attached to the outside of reservoir 204 within cassette 250 separated by a distance d as shown at point 304. The present design may electrically connect plate 302 to electric circuit 350 at point 351 and plate 303 may connect at point 352. The connections may be realized using a pogo pin male type connector, or equivalent connector, configured to plug into a companion pogo pin female connector provided as part of instrument host 102 circuit 350. However, any connection known in the art may be used. Electric circuit 350 may include electrical components, such as passive devices such as resistors and active devices such as diodes connected to a signal source, such as a square-wave generator to drive the circuit between the two plates. Driving the electric circuit in this manner may allow for measuring the amount of electric charge stored, or capacitance, by the plate pair capacitor arrangement inside reservoir 204.

System 300 may sense and determine the fluid level within reservoir 204 in relation to the amount of charge measured between the present design's plate pair, plate 302 and plate 303. The plate pair may be integrated with reservoir 204 by spraying or coating a conductive paint on the inside or outside of reservoir 204. Alternatively, the plates may be implemented by applying conductive tape, such as copper with an adhesive backing, to the inside or outside of reservoir 204. Furthermore, the plates may be implemented as conductive surfaces in close proximity to reservoir 204 but built into the surgical instrument. Other connection methods may be employed, including but not limited to suspending the plates in reservoir 204.

The present design may include an electric circuit 350 to exhibit a typical resistor-capacitor (RC) circuit. The voltage in an RC circuit changes in response to changes in capacitance and may be determined using the following formula:

$$V_o = V_I * (1 - e^{-t/RC}) \quad (2)$$

where $V_o$ is the measured voltage between the top of plate 302 and the bottom of plate 303 as illustrated in FIG. 3A. Continuing on with equation (2), $V_I$ is the voltage of the square wave applied across the plates, R is the resistance of a resistor configured in series with the plate pair, C is the plate capacitance, and t equals time. Configuring an RC circuit in this manner may allow the present design to measure the RC voltage response of circuit 350 and thus determine the capacitance using Equation (2).

Capacitive fluid level sensing system 300 may measure the capacitance resulting from at least one plate pair using electric circuit 350 and communicate a signal, for example the voltage response, indicating an increase or decrease in capacitance to instrument host 102 as a result of an increase or decrease in fluid shown at 310. Instrument host 102 may control a pump to operate and move fluid from the reservoir to the collector based on a communicated increase in capacitance, preset maximum threshold, or capacitance change rate. Similarly, the instrument host 102 may control a pump to operate and move fluid from the collector to the reservoir based on a communicated decrease in capacitance, preset minimum threshold, or capacitance change rate.

FIG. 3B illustrates a capacitive fluid level sensing system 300 for a surgical cassette 250 reservoir 204 including electric circuit 350 where a single pair of plates, i.e. two conductors, forms a capacitor. The illustration of FIG. 3B shows two interleaved conductive plates oriented as illustrated in FIG. 3B. The plates in FIG. 3B are termed stepped plates, where stepped plates comprise a main or base plate oriented at one angle with plate steps or protrusions oriented orthogonally to the main or base plate as shown. Operation may be as discussed above, wherein system 300 and the circuitry shown may sense and determine the fluid level within reservoir 204 in relation to the amount of charge measured between interleaved plate 305 and plate 306.

FIG. 3C illustrates a further capacitive fluid level sensing system 300 where three pairs of conductive plates form three distinct capacitors. The present design may orient the three pairs in a horizontal direction, each pair comprising two parallel plates, each pair at differing heights within reservoir 204 as illustrated n FIG. 3C.

In one embodiment, capacitive fluid level sensing system 300 may fix or attach a first set of plates 309, a mid level set of plates 308, and a third lower level positioned set of plates 307 to the inside of reservoir 204 within cassette 250 separated in a multiple height configuration. Sets of plates 307, 308, and 309 may be electrically connected to electric circuit 355 at 356 as shown in FIG. 3C. Driving the electric circuit in the manner as previously described for FIG. 3A may allow for measuring the amount of electric charge stored, or capacitance, at each plate pair arrangement configured inside reservoir 204. System 300 may sense the fluid level within reservoir 204 in relation to the amount of charge measured between the present designs plates at 309, 308, and 307 as previously described for electric circuit 350.

In this configuration, indicating the fluid level has fallen below set of plates 307, 308, or 309, capacitive fluid sensing system 300 may measure the capacitance resulting from multiple plate pairs using electric circuit 355 and communicate a signal indicating a change (e.g. an increase or decrease in capacitance) at each measurement height to instrument host 102 as a result of an increase or decrease in fluid shown by arrow 310. The present design may individually detect capacitance at each plate pair, using individual measuring circuits, to indicate when fluid has reached and covered the plates.

The plate pairs can alternately be connected to form a single capacitor resulting in step changes in capacitance as the fluid covers or uncovers each plate pair as the fluid level rises or falls. Instrument host 102 may control a pump, such as a peristaltic pump, to operate and move fluid from reservoir 204 to the collector based on a communicated capacitance at each height. For example, if all three capacitors report a low capacitance value to instrument host 102, the host may determine that the fluid level is low and may control the peristaltic pump to operate and move fluid from the collector or other fluid source to reservoir 204.

The previously described embodiments disclose designs that attach capacitive plates internally and/or externally to the reservoir. Designs that involve placement of plates, attached inside or outside of the reservoir, may reduce reliability and potentially become unsafe. Reliability in these designs may be reduced by the need to provide electrical connections from the plates within the cassette to the electric circuit. Designs that involve placement of the plates inside the reservoir may potentially complete a direct connection formed between the patient and conductive fluid to the electronics, which can be undesirable. In order to provide a reliable and safe design, and to reduce total cost, the present design may involve configuring the capacitive plates with and as part of the instrument host system. The plates may therefore be integrated in the instrument host system and may be arranged in close proximity to the holding mechanism, or cavity, where the cassette is located. This eliminates the need for electrical connections within the reservoir.

FIG. 3D illustrates the horizontal cross-section for one such integrated system where a fluid chamber 385, such as a reservoir similar to reservoir 204 shown in FIG. 2A, forms part of the cassette design. The present design may fix plate pair 360, 370 on the outside of fluid chamber 385 as shown in FIG. 3D, where chamber wall 380 is shown, and an electrical connection may be provided between the plates and the electric circuit within instrument host 102 (not shown in FIG. 3D).

In the illustration of FIG. 3D, the system may include plates 360, 370 on the outside of a small cavity associated with instrument host 102 configured to hold fluid chamber 385 flush between the plate pair once inserted into the cavity by an operator. Flush mounting fluid chamber 385 in this manner may minimize the distance between the plates and maximize the change in capacitance observed while mitigating the need for unreliable electrical connections by using permanent connections between the plates and electric circuit configured with instrument host 102. In this configuration, as fluid rises in fluid chamber 385, or reservoir, the capacitance formed between plates 360, 370 increases, and conversely, as fluid falls in fluid chamber 385, the capacitance decreases between plates 360, 370.

Figure 3E:
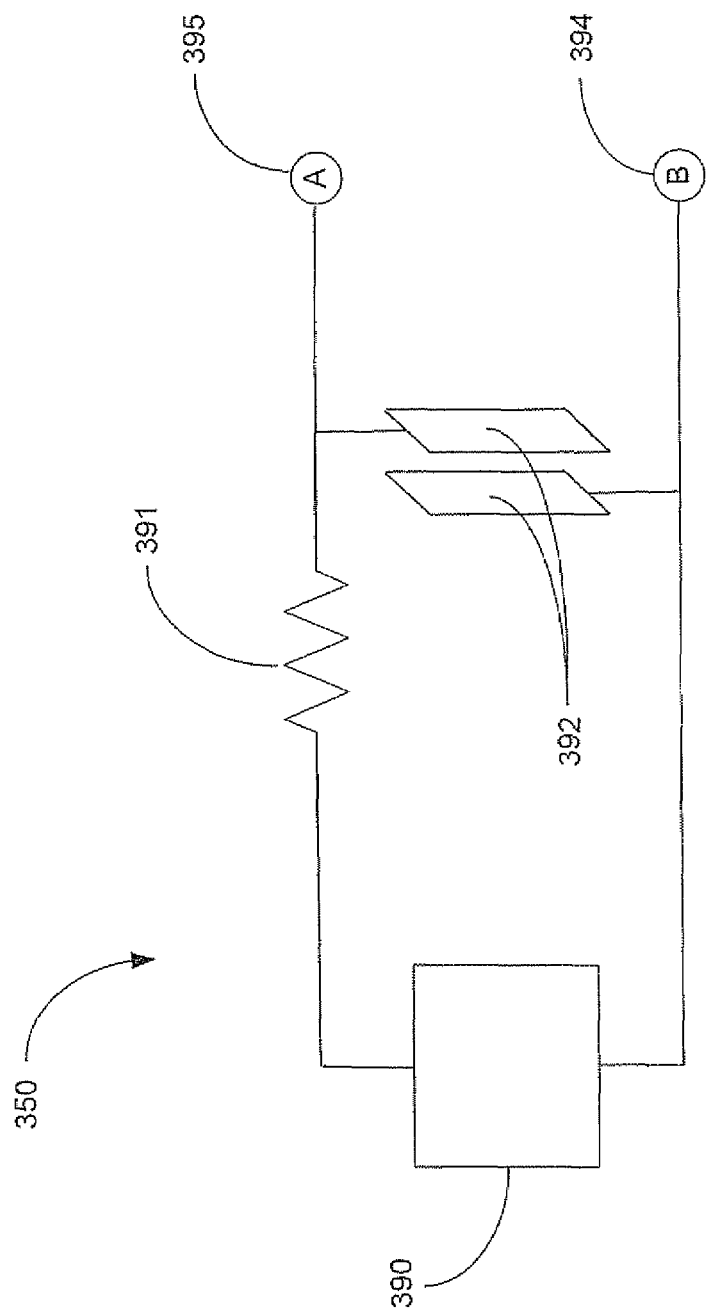
FIG. 3E illustrates an exemplary electric circuit configured as a RC circuit in accordance with an aspect of the present design.

FIG. 3E illustrates an exemplary electric circuit 350 configured as a RC circuit in accordance with an aspect of the present design. The present design may arrange a resistor 390 and a signal source 391 with two conductive plates 392. The voltage response for electric circuit 350 is measured between 'A' at point 395 and point 'B' at point 394.

Figure 3F:
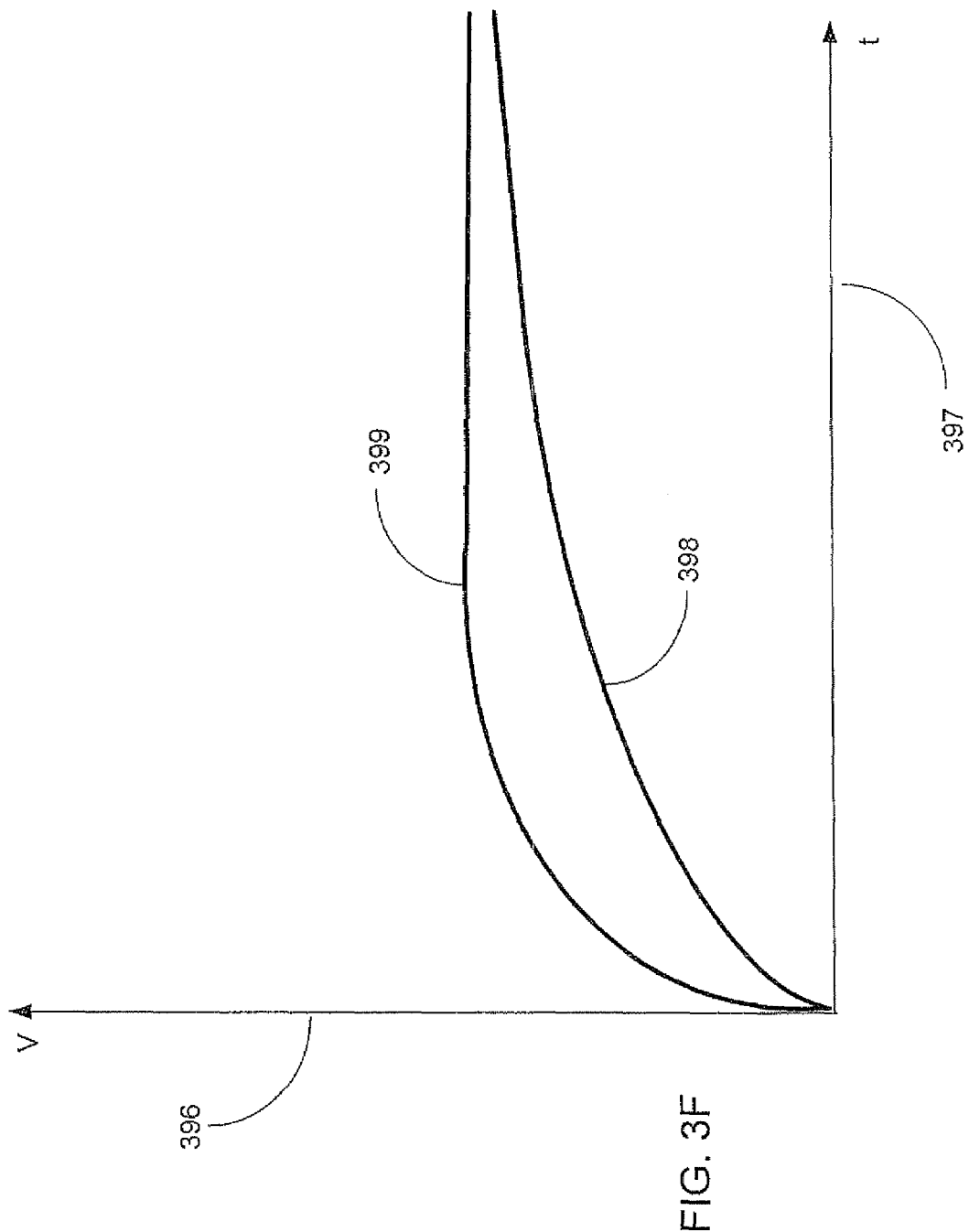
FIG. 3F illustrates an approximate voltage response for the present design electric circuit in accordance with an aspect of the present design.

An approximate voltage response for the capacitive sensor is illustrated in FIG. 3F. The response is plotted as voltage (on axis 396) versus time (on axis 397). The response curve for plates submerged by fluid is shown as response 398 and the voltage response for plates in air is shown as response 399. Measurements for a pair of conductive plates in air versus submerged in BSS yield approximately a 2 to 1 change in the observed capacitance.

Figure 3G:
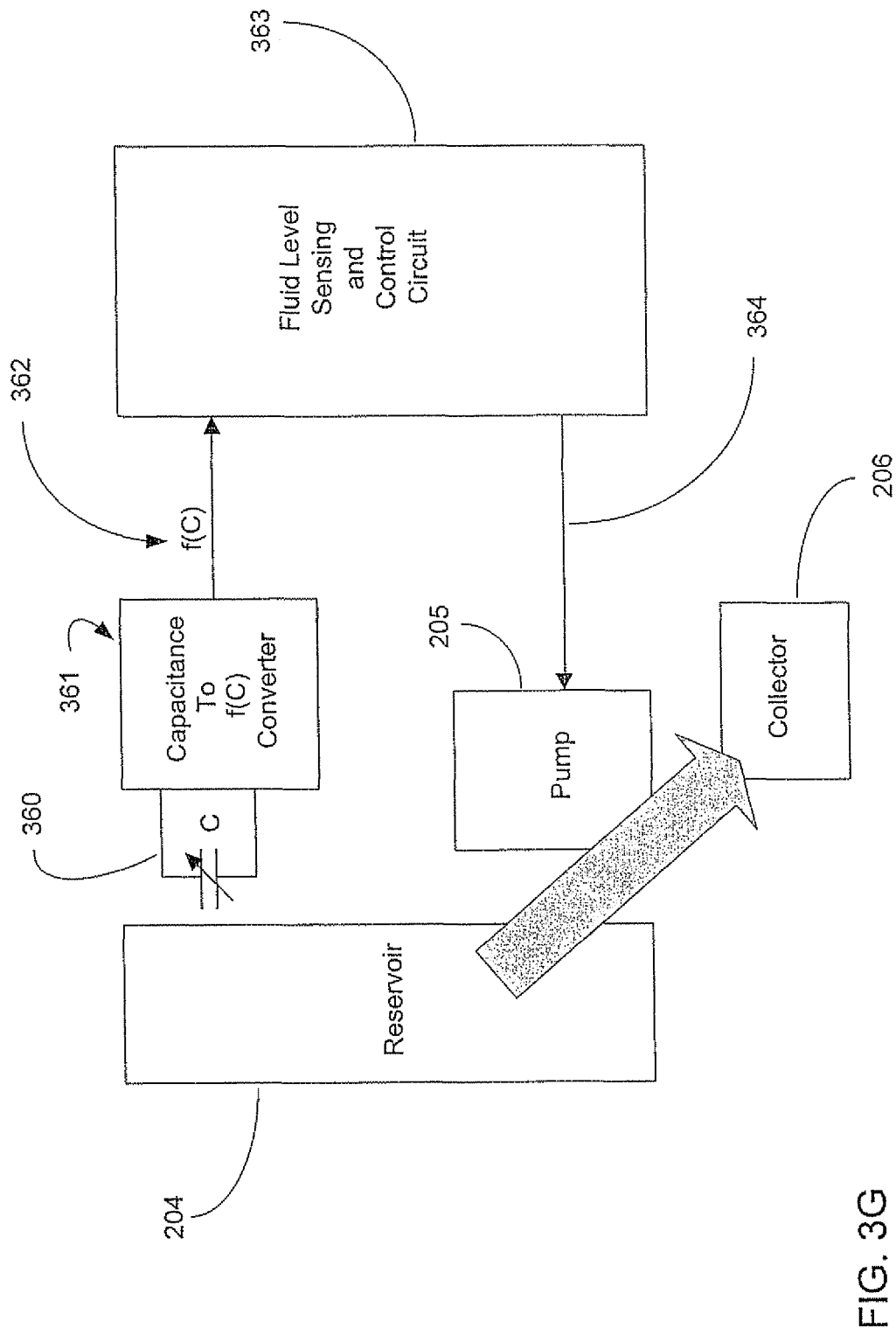
FIG. 3G illustrates an exemplary electric circuit configured in accordance with an aspect of the present design.

Electrical circuits may be configured to measure capacitance using an oscillator circuit arranged to vary output frequency in relation to changes in input capacitance at the plate pair. FIG. 3G illustrates an exemplary fluid level sensing system that may involve capacitive plates to realize variable capacitor 360 and may connect variable capacitor 360 to a capacitance to frequency converter 361. Converter 361 may vary frequency output signal 362 (f(C)) in response to the capacitance measured at capacitor 360. Fluid level sensing and control circuit 363 may receive frequency output signal 362 and based on this frequency output signal may operate pump 205 by turning it on or off using a control signal transmitted over line 364. When control circuit 363 processes frequency output signal 362 and turns on pump 205, fluid is removed from reservoir 204 and moved to collector 206 as previously described.

Additional circuits may include, but are not limited to, varying output voltage, current, pulse width, or duty cycle in response to changes in input capacitance or a constant current charge measuring circuit.

Although the capacitive plate pair represented in FIGS. 3A, 3C, 3D, and 3E illustrate or suggest a rectangular shape for the plates, the shape of the plates are not limited to geometric or rectangular shapes, and may be realized using customized shapes. The illustrations that form FIGS. 3A-D are generally not drawn to scale and are for illustrative purposes.

Figure 4A:
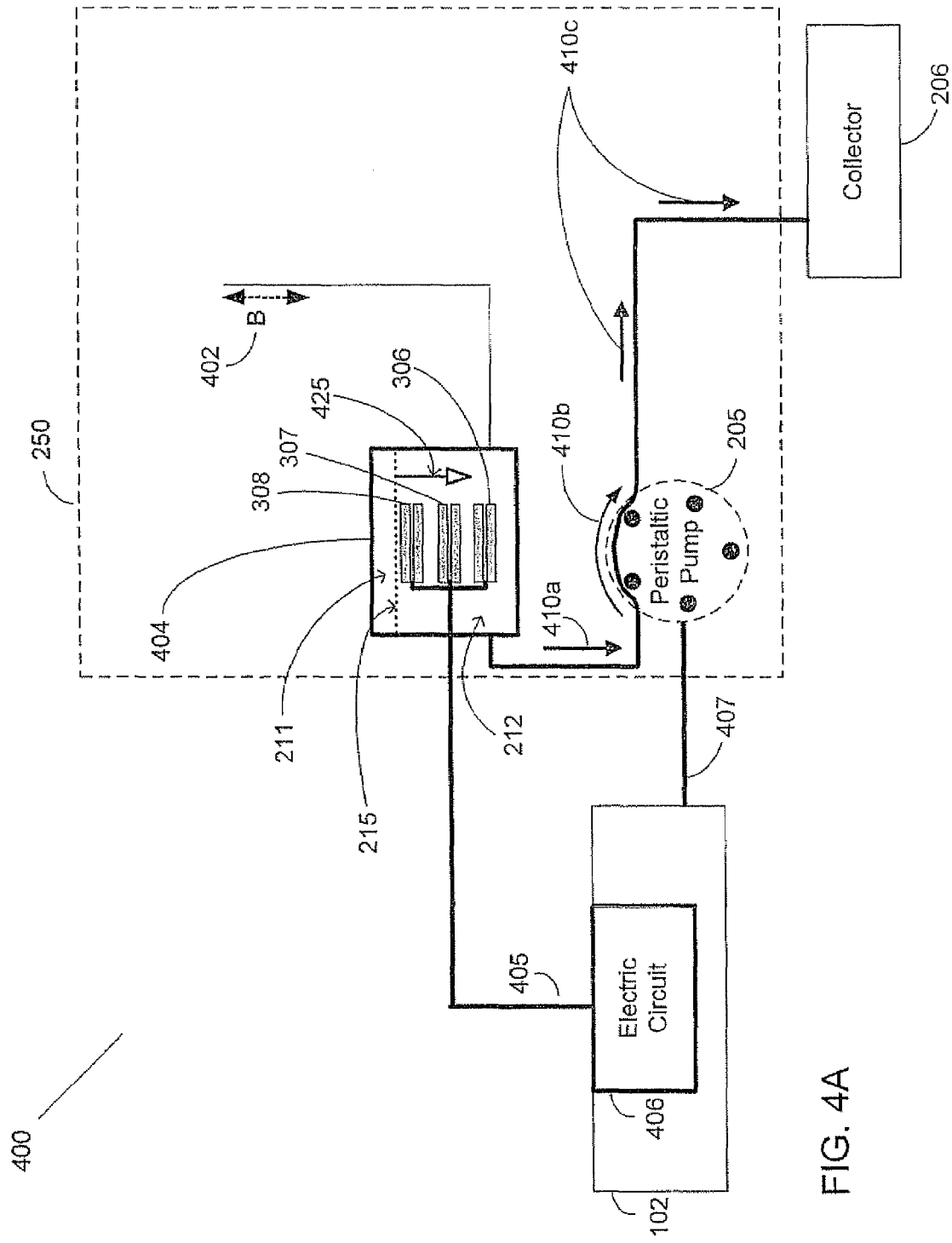
FIG. 4A is a functional block diagram illustrating a surgical cassette system configured for peristaltic pump outflow operation in accordance with the present design.
Figure 4B:
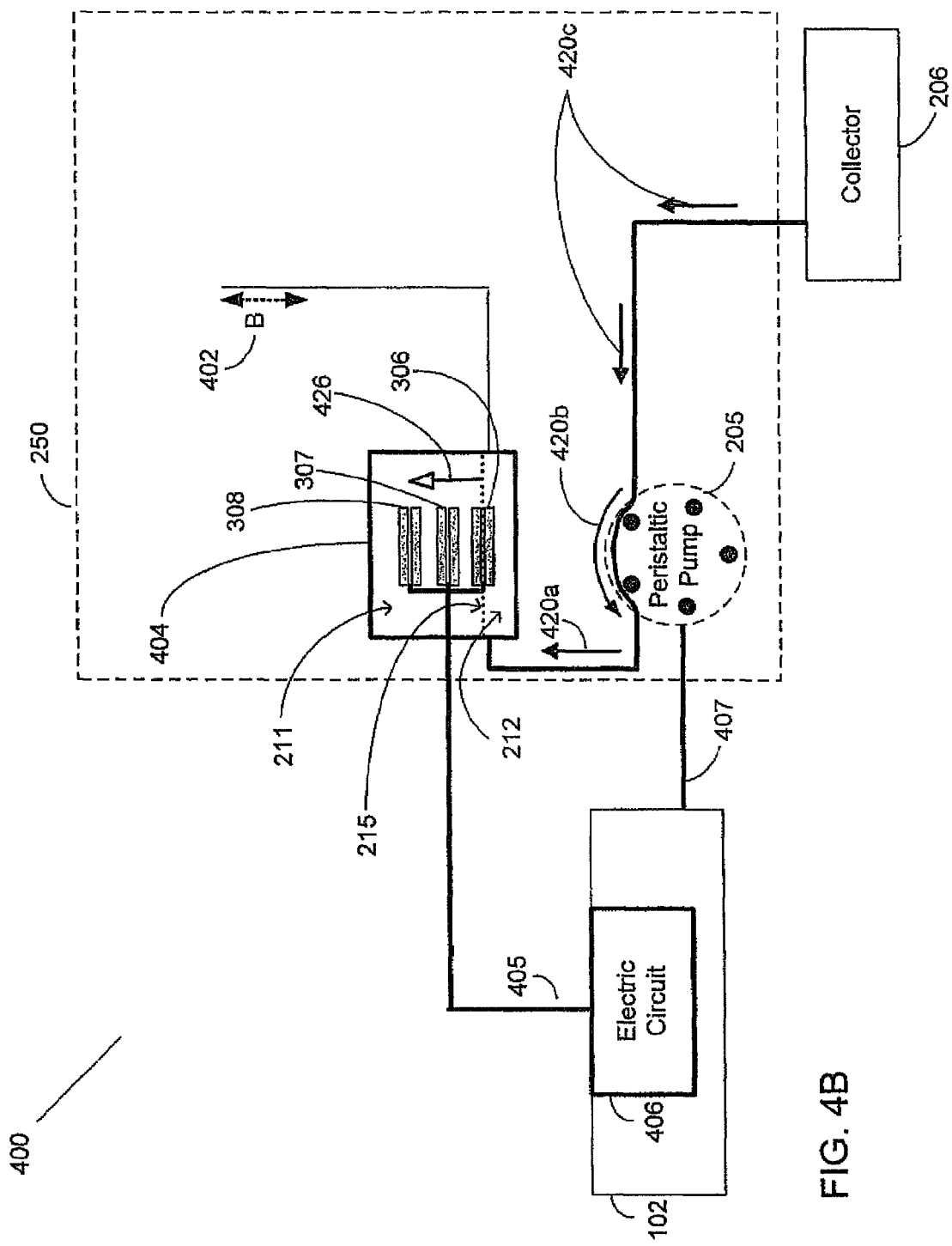
FIG. 4B is a functional block diagram illustrating a surgical cassette system configured for peristaltic pump inflow operation in accordance with the present design.

FIGS. 4A and 4B illustrate two modes of operation for the present design. The first mode is illustrated in FIG. 4A, where capacitive fluid sensing system 400 with surgical cassette 250 may employ peristaltic pump 205 to move fluid from reservoir 404 to collector 206 as a result of a high level of fluid in reservoir 404. In this arrangement, plate pairs 306, 307, and 308 all may report a high capacitance to electric circuit 406 via a connection 405 due to fluid covering the three plate pairs. Electric circuit 406 may convert the reported capacitance into a voltage response sufficient to indicate to instrument host 102 to operate peristaltic pump 205 via connection 407 to pump fluid from reservoir 404 to collector 206.

As instrument host 102 runs pump 205, the amount of fluid decreases as indicated by arrow 425. As the fluid decreases and plate pair 308 is exposed to air in air space 211, the capacitance reported to instrument host 102 decreases. As the fluid level drains below plate pair 307, the reported capacitance further decreases. When air-fluid boundary 215 is reduced below plate pair 306, the reported capacitance may fall below a certain threshold indicating reservoir 404 is drained and the instrument host may stop pump 205. Operating pump 205 may move fluid from reservoir 404 to collector 206 along the path indicated by arrows 410a, b, and c. General fluid flow to other parts of the design is shown as arrow B 402.

The second mode is illustrated in FIG. 4B where capacitive fluid sensing system 400 with surgical cassette 250 may configure peristaltic pump 205 for pumping or moving of fluid from collector 206 and/or fluid pathways between collector 206 and reservoir 404, to reservoir 404 due to a low level of fluid in reservoir 404. In this arrangement, plate pairs 306, 307, and 308 all may report a low capacitance to electric circuit 406 via a connection 405 when air-fluid boundary 215 is below plate pair 306. Electric circuit 406 may convert the reported capacitance into a voltage response sufficient to indicate to instrument host 102 to operate peristaltic pump 205 via connection 407 in a counter clock-wise direction 420b to pump fluid from collector 206 and/or fluid pathways between collector 206 and reservoir 404, to reservoir 404.

As instrument host 102 runs pump 205, the amount of fluid increases as indicated by arrow 426. As the fluid level increases and rises above plate pair 306, the reported capacitance increases. As the fluid level rises above plate pair 307, the reported capacitance further increases. When air-fluid boundary 215 rises above plate pair 308, the reported capacitance may rise above a certain threshold indicating reservoir 404 is full. Operating pump 205 may move fluid from collector 206 to reservoir 404 along the path indicated by arrows 420a, b, and c as illustrated in FIG. 4B. Again, general fluid flow to other parts of the design is shown as arrow B 402.

In sum, the present design of a capacitive fluid level sensing system provides for automatic draining or filling of fluid within a reservoir during an ocular procedure by operating a pump, for example a vacuum, venturi, or peristaltic pump, using capacitive sensing. The present design does not require a fluid float mechanism and thus is free of incorrect measurements due to a stuck or "sunk" float condition. Further, the presence of BSS beads and condensation on the sides of the reservoir tank that make optical level detection difficult generally do not sufficiently alter the measured capacitance because the fluid volume between the plates is not significantly changed.

In general, automatic or semi-automatic operation entails sensing a change in capacitance and either drains fluid from the reservoir or pumps fluid into the reservoir. In any circumstance, the surgeon or other personnel are provided with the ability to run the pumps in any available direction, such as for cleaning purposes.

Other pumping states may be provided as discussed herein and may be employed based on the desires of personnel performing the surgical procedure. Other configurations may be provided, including limiting the voltage response of the capacitive sensing device to be within a desired range, and so forth.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A medical device, comprising:
    a plurality of pairs of conductive plates electrically connected in parallel and forming a sensor positioned within a fluid maintaining device associated with the medical device; and
    a controller configured to receive data from the plurality of conductive plates forming the sensor;
    wherein the plurality of pairs of conductive plates are configured to sense fluid changes in the fluid maintaining device, each conductive plate has a planar shape, and the plurality of pairs of conductive plates are configured to provide data to the controller based on the sensed fluid changes, wherein the controller is configured to facilitate fluid evacuation from and fluid infusion to the fluid maintaining device associated with the medical device based on data received from the plurality of pairs of conductive plates and the equation:

$$V_O(p) = V_I(p) * (1 - e^{-t/RC})$$

where $V_O(p)$ is the measured voltage between the pair of conductive plates, $V_I(p)$ is the voltage of a square wave provided across the pair of conductive plates, R is resistance of a resistor configured in series with the pair of conductive plates, C is capacitance of the pair of conductive plates, and t is time.

2. The medical device of claim 1, wherein the plurality of pairs of conductive plates comprises at least three pairs of conductive plates.

3. The medical device of claim 1, wherein the fluid maintaining device comprises a reservoir housed within a cassette.

4. The medical device of claim 1, wherein the fluid maintaining device comprises a reservoir, and wherein the plurality of pairs of conductive plates are at least partially disposed within fluid when the reservoir contains.

5. The medical device of claim 1, wherein the fluid maintaining device comprises a reservoir, and the plurality of pairs of conductive plates are positioned within the reservoir located within the medical device.

6. The medical device of claim 1, wherein the fluid maintaining device comprises a reservoir, and the plurality of pairs of conductive plates are integrated with the medical device and positioned in close proximity to the reservoir configured to be positioned within the medical device.

7. The medical device of claim 1, wherein the plurality of pairs of conductive plates and controller are configured to sense an increased fluid level in the fluid maintaining device and evacuate fluid from the fluid maintaining device subsequent to sensing the increased fluid level.

8. The medical device of claim 1, wherein the plurality of pairs of conductive plates forms a capacitive sensor wherein capacitance is proportional to permittivity of dielectric material between plates, wherein the dielectric material comprises the fluid.

9. The medical device of claim 1, wherein the plurality of pairs of conductive plates and controller are configured to sense a decreased fluid level in the fluid maintaining device, causing at least one selected from the group consisting of:
    termination of fluid removal; and
    providing fluid to the fluid maintaining device subsequent to sensing the decreased fluid level.

10. The medical device of claim 1, wherein the plurality of pairs of conductive plates comprises at least two pairs of conductive plates.

11. The medical device of claim 1, wherein the medical device is an ophthalmic surgical device.

12. The medical device of claim 11, wherein the ophthalmic surgical device is a phacoemulsification system.

13. A fluid level sensing arrangement, comprising:
    a plurality of pairs of conductive plates electrically connected in parallel and positioned within a fluid maintaining device, wherein each conductive plate is planar in shape; and
    a controller electrically connected to the plurality of pairs of conductive plates;
    wherein the controller is configured to sense electrical changes in the plurality of pairs of conductive plates based on different volumes of fluid and selectively provide fluid to and evacuate fluid from the fluid maintaining device based on the controller sensing electrical changes at the plurality of pairs of conductive plates, wherein the controller selectively provides fluid to and evacuate fluid from the fluid maintaining device based on the equation:

$$V_O(p) = V_I(p) * (1 - e^{-t/RC})$$

where $V_O(p)$ is the measured voltage between the pair of conductive plates, $V_I(p)$ is the voltage of a square wave provided across the pair of conductive plates, R is resistance of a resistor configured in series with the pair of conductive plates, C is capacitance of the pair of conductive plates, and t is time.

14. The fluid level sensing arrangement of claim 13, wherein the plurality of pairs of conductive plates are employed to sense different fluid levels in the fluid maintaining device.

15. The fluid level sensing arrangement of claim 13, wherein the plurality of pairs of conductive plates is at least partially disposed within fluid when the fluid maintaining device contains fluid.

16. The fluid level sensing arrangement of claim 13, wherein the plurality of pairs of conductive plates and controller are configured to sense an increased fluid level in the fluid maintaining device and evacuate fluid from the fluid maintaining device subsequent to sensing the increased fluid level.

17. The fluid level sensing arrangement of claim 13, wherein the plurality of pairs of conductive plates form a capacitive sensor wherein capacitance is proportional to permittivity of dielectric material between plates, wherein the dielectric material comprises the fluid.

18. The fluid level sensing arrangement of claim 13, wherein the plurality of pairs of conductive plates and controller are configured to sense a decreased fluid level in the fluid maintaining device and cause fluid to be provided to the fluid maintaining device subsequent to sensing the decreased fluid level.

19. The fluid level sensing arrangement of claim 13, wherein the plurality of pairs of conductive plates comprises at least two pairs of conductive plates.

20. The fluid level sensing arrangement of claim 13, wherein the fluid level sensing arrangement is part of an ophthalmic surgical device.

21. The fluid level sensing arrangement of claim 20, wherein the ophthalmic surgical device is a phacoemulsification system.

22. A surgical system, comprising:
a controller configured to receive electrical signals and effectuate controlled functionality of the surgical system;
a reservoir configured to contain fluid usable in performing a medical procedure;
a capacitive sensing device located within the reservoir and configured to sense fluid level in the reservoir, wherein the capacitive sensing device comprises a plurality of pairs of planar conductive plates; and
electrical connections between the controller and the capacitive sensing device, wherein the plurality of pairs of planar conductive plates are connected in parallel;
wherein the capacitive sensing device is configured to sense changes in fluid level in the reservoir, convey sensed changes to the controller via the electrical connections, and the controller is configured to selectively alter fluid level in the reservoir based on the equation:

$$V_O(p) = V_I(p) * (1 - e^{-t/RC})$$

where $V_O(p)$ is the measured voltage between the pair of planar conductive plates, $V_I(p)$ is the voltage of a square wave provided across the pair of planar conductive plates, R is resistance of a resistor configured in series with the pair of planar conductive plates, C is capacitance of the pair of planar conductive plates, and t is time.

23. The surgical system of claim 22, wherein the capacitive sensing device comprises at least three pairs of planar conductive plates.

24. The surgical system of claim 23, wherein the capacitive sensing device is employed to sense different fluid levels in the reservoir.

25. The surgical system of claim 22, wherein the capacitive sensing device is positioned in association with the reservoir.

26. The surgical system of claim 22, wherein the capacitive sensing device is at least partially disposed within fluid when the reservoir contains fluid.

27. The surgical system of claim 22, wherein the capacitive sensing device and controller are configured to sense an increased fluid level in the reservoir and evacuate fluid from the reservoir subsequent to sensing the increased fluid level.

28. The surgical system of claim 22, wherein the capacitive sensing device is configured to sense capacitance and the capacitance is proportional to permittivity of dielectric material between the plurality of pairs of planar conductive plates, wherein the dielectric material comprises the fluid.

29. The surgical system of claim 22, wherein the capacitive sensing device and controller are configured to sense a decreased fluid level in the reservoir, causing at least one selected from the group consisting of:
termination of fluid removal; and
providing fluid to the reservoir subsequent to sensing the decreased fluid level.

30. The surgical system of claim 22, wherein the plurality of pairs of planar conductive plates comprises at least two pairs of planar conductive plates.

31. The surgical system of claim 22, wherein the surgical system is used during an ocular surgical procedure.

32. The surgical system of claim 31, wherein the ocular surgical procedure is phacoemulsification.

* * * * *